United States Patent [19]

Saho et al.

[11] Patent Number: 5,047,491
[45] Date of Patent: Sep. 10, 1991

[54] POLYORGANOSILOXANE COMPOUNDS

[75] Inventors: Takahiro Saho; Yoshinori Akutsu; Takaharu Nakano; Nobumasa Ohtake, all of Yokohama, Japan

[73] Assignee: Chisso Corporation, Japan

[21] Appl. No.: 388,076

[22] Filed: Aug. 1, 1989

[30] Foreign Application Priority Data

Aug. 1, 1988 [JP] Japan .................................. 63-192316

[51] Int. Cl.$^5$ ............................................. C08G 77/06
[52] U.S. Cl. ......................................... 528/15; 528/42; 528/31; 528/32; 528/29; 556/479; 556/485
[58] Field of Search ...................... 528/42, 15, 31, 32, 528/29; 556/479, 485

[56] References Cited

U.S. PATENT DOCUMENTS

| | | | |
|---|---|---|---|
| 3,328,450 | 6/1967 | Plueddemann | 260/448.8 |
| 3,423,445 | 1/1969 | Holbrook | 260/448.2 |
| 3,462,386 | 8/1969 | Gossens | 260/37 |
| 4,574,149 | 3/1986 | Lee et al. | 528/42 |
| 4,658,049 | 4/1987 | Nakano et al. | 556/437 |
| 4,748,225 | 5/1988 | Yoshioka et al. | 528/29 |
| 4,920,184 | 4/1990 | Schäfer et al. | 525/477 |

FOREIGN PATENT DOCUMENTS 274103 7/1988 European Pat. Off. .
277816 8/1988 European Pat. Off. .

*Primary Examiner*—Melvyn I. Marquis
*Assistant Examiner*—Margaret W. Glass
*Attorney, Agent, or Firm*—Leydig, Voit & Mayer

[57] ABSTRACT

A polyorganosiloxane compound is provided which has a fluorine-containing group at its $\alpha$-position and one or more than one hydrosilyl group at its $\omega$-position, has a fluorine-containing group located at least at its $\alpha$- and $\alpha'$-position and one or more than one hydrosilyl group at its $\omega$-position or has a fluorine-containing group at least at its $\alpha$-, $\alpha'$- and $\alpha''$-position and one or more than one hydrosilyl group at its $\omega$-position.

24 Claims, No Drawings

POLYORGANOSILOXANE COMPOUNDS

BACKGROUND OF THE INVENTION

1. Field of the Invention

The present invention relates to a novel polyorganosiloxane compound suitable for modifying synthetic resins.

2. Description of Related Art

Heretofore, silicone resins have been employed for providing synthetic resin molded products with various characteristics such as surface properties including water repellency, mold releasability and antifouling properties inherent in siloxane compounds as well as thermal resistance. These silicone resins are mainly composed of linear polysiloxane compounds. The linear polysiloxane compounds are blended if they do not possess a group or groups reactive with the resins while they are chemically introduced into the resins if they possess a group or groups reactive therewith.

Increasing attention has recently been paid to polysiloxane compounds for use as raw materials of graft polymers for modifying synthetic resins. As such polysiloxane compounds have been mainly employed so-called "polysiloxane compounds modified at one terminal" in which a reactive group resides at only one of their terminals and a trimethylsiloxy group resides at the other terminal.

When the polysiloxane compounds are used with the attempt to improve characteristics of synthetic resins, improvements in characteristics of the synthetic resins rely primarily upon functions inherent in the polysiloxane compounds in order to satisfy recent demands for higher functional characteristics. Therefore, it poses the difficulties that insufficient improvements have been achieved or a large quantity of the polysiloxanes should be added to achieve characteristics sought to be performed by addition, thereby adversely affecting other characteristics.

When there is used a polysiloxane compound wherein its both terminals are provided with the same substituents i.e., a so-called "polysiloxane compound modified at both terminals", which are not reactive with the objective synthetic resin, it suffers the disadvantages that the amount of the polysiloxane compound to be added cannot be increased on account of bleeding and fluctuations in characteristics may occur to a remarkably large extent as time elapses, whereby the expected characteristics cannot be maintained for a long period of time.

On the contrary, when the polysiloxane modified at both terminals is used in which groups substituents reactive with the synthetic resins are used for their surface modifications, it also poses the difficulty that a large amount of the polysiloxane compound should be added, thereby resulting in a remarkable reduction in other properties. Furthermore, it is difficult to use the polysiloxane compound modified at both terminals as a graft polymer which has recently drawn increasing attention for modifying surfaces of the synthetic resins.

In the polysiloxane compound modified at its one terminal, a group at its one terminal which is not reactive with the synthetic resins is generally constituted a trimethylsiloxy group, and modifications of characteristics for the synthetic resins are dependent upon the properties of the polysiloxane compound. Therefore, demands for higher functions are not achieved to a sufficient extent or a large amount of the polysiloxane compound should be added in order to satisfy the characteristics sought to be attained, thus adversely affecting other properties.

It is further to be noted that dimethylsiloxane alone, in which its terminal is terminated by means of the trimethylsiloxy group, can little improve an oil repellency.

SUMMARY OF THE INVENTION

Therefore, the present invention has the object to provide a novel polyorganosiloxane compound having a fluoroalkyl group at one terminal and a reactive group at the other terminal, which can improve the difficulties and problems prevailing in conventional polysiloxane compounds.

In order to achieve the above-mentioned object, the present invention comprises a polyorganosiloxane compound in which a fluorine-containing substituent is located at least at an α-position, at α- and α'-positions or at α-, α'- and α"-positions and at least one hydroxyl group at an ω-position.

In accordance with the present invention, the first feature is directed to a polyorganosiloxane compound represented by the following general formula (I):

$$R^1 \left[ \begin{array}{c} CH_3 \\ | \\ Si-O \\ | \\ CH_3 \end{array} \right]_j \begin{array}{c} R^3 \\ | \\ Si-R^2 \\ | \\ R^4 \end{array} \quad (I)$$

in which
j is an integer from 2 to 2,000;
$R^1$ is a pentafluorophenyl group or a linear or branched fluoroalkyl group as represented by the following general formula (II):

$$C_aH_bF_{2a-b+1} \quad (II)$$

(wherein
a is an integer from 3 to 18; and
b is 0 or an integer of 2a)
$R^2$ is 3-(m-hydroxyphenyl)propyl group, 3-(o-hydroxyphenyl)propyl group, 3-(p-hydroxyphenyl)propyl group, a substituent as represented by the general formula (III):

$$-(CH_2)_{h0}-(OCH_2CH_2)_{h1}-(OCHCH_2)_{h2}-OH \quad (III)$$
$$\hspace{4cm} | \\ \hspace{4cm} CH_3$$

(wherein
$h^0$ is an integer from 1 to 6; and
$h^1$ and $h^2$ are independently each 0 or an integer from 1 to 20), a substituent a represented by the following general formula (IV):

$$\begin{array}{l} -(CH_2CH_2O)_{h1}-(CHCH_2O)_{h2}-(CH_2)_{h0}- \\ \hspace{2.5cm} | \hspace{2.5cm} | \\ \hspace{2.5cm} X^1 \hspace{2.5cm} CH_3 \\ -OCH_2CCH_2(OCH_2CH_2)_{h3}(OCHCH_2)_{h4}-OH \\ \hspace{0.5cm} | \\ \hspace{0.5cm} (OCH_2CH_2)_{h5}(OCHCH_2)_{h6}-OH \\ \hspace{3cm} | \\ \hspace{3cm} CH_3 \end{array} \quad (IV)$$

(wherein
X$^1$ is a hydrogen atom, methyl group or ethyl group;
h$^3$, h$^4$, h$^5$ and h$^6$ are independently 0 or an integer from 1 to 20; and
h$^0$, h$^1$ and h$^2$ have the same meanings as above), or a substituent as represented by the following general formula (V):

$$\left[-(CH_2CH_2O)_{h1}-(CHCH_2O)_{h2}-(CH_2)_{h0}- \atop \underset{OCH_2CCH_2(OCH_2CH_2)_{h3}(OCHCH_2)_{h4}-OH}{X^2} \atop \underset{CH_2(OCH_2CH_2)_{h5}(OCHCH_2)_{h6}-OH}{} \atop CH_3 \right] \quad (V)$$

(wherein
X$^2$ is a hydrogen atom, methyl group or ethyl group; and
h$^0$, h$^1$, h$^2$, h$^3$, h$^4$, h$^5$ and h$^6$ have the same meanings as above); and
R$^3$ and R$^4$ are independently each an alkyl group having from 1 to four carbon atoms or a phenyl group.

The second feature of the present invention is directed to a polyorganosiloxane compound in which the substituent represented by the symbol R$^1$ is 3,3,3-trifluoropropyl group, tridecafluoro-1,1,2,2-tetrahydrooctyl group or heptadecafluoro-1,1,2,2-tetrahydrodecyl group.

The third feature of the present invention is directed to a polyorganosiloxane compound as represented by the following general formula (VI):

$$R^5-\left[\begin{array}{c}CH_3 \\ | \\ Si-O \\ | \\ CH_3\end{array}\right]_k \begin{array}{c}R^7 \\ | \\ Si-R^2 \\ | \\ \end{array} \atop R^6-\left[\begin{array}{c}CH_3 \\ | \\ Si-O \\ | \\ CH_3\end{array}\right]_l \quad (VI)$$

in which
k and l each is an integer from 2 to 2,000;
R$^5$ and R$^6$ are independently each an alkyl group having from 1 to 4 carbon atoms, pentafluorophenyl group or a linear or branched fluoroalkyl group as represented by the above-mentioned general formula (II): provided, however, that at least one of R$^5$ and R$^6$ is the pentafluorophenyl group or the fluoroalkyl group;
R$^2$ has the same meaning as mentioned above;
R$^7$ is an alkyl group having 1 to four carbon atoms or a phenyl group.

The fourth feature of the present invention is directed to a polyorganosiloxane compound of the above third feature in which the substituents represented by the symbols R$^5$ and R$^6$ in the general formula (VI) are independently each an alkyl group having 1 to four carbon atoms, 3,3,3-trifluoropropyl group, tridecafluoro-1,1,2,2-tetra-hydrooctyl group or heptadecafluoro-1,1,2,2-tetrahydro-decyl group.

In accordance with the present invention, the fifth feature is directed to a polyorganosiloxane compound as represented by the following general formula (VII):

$$R^8-\left[\begin{array}{c}CH_3 \\ | \\ Si-O \\ | \\ CH_3\end{array}\right]_m \atop R^9-\left[\begin{array}{c}CH_3 \\ | \\ Si-O \\ | \\ CH_3\end{array}\right]_n-Si-R^2 \atop R^{10}-\left[\begin{array}{c}CH_3 \\ | \\ Si-O \\ | \\ CH_3\end{array}\right]_p \quad (VII)$$

in which
m, n and p each independently is an integer from 2 to 2,000;
R$^8$, R$^9$ and R$^{10}$ are independently each an alkyl group having from 1 to 4 carbon atoms, a pentafluorophenyl group or a linear or branched fluoroalkyl group as represented by the above-mentioned general formula (II): provided, however, that at least one of R$^8$, R$^9$ and R$^{10}$ is the pentafluorophenyl group or the fluoroalkyl group;
R$^2$ is the same meaning as mentioned above;

The sixth feature of the present invention is directed to a polyorganosiloxane compound of the above fifth feature in which the substituents as represented by the reference symbols R$^8$, R$^9$ and R$^{10}$ of the general formula (VII) are independently each an alkyl group having from 1 to four carbon atoms, 3,3,3-trifluoropropyl, tridecafluoro-1,1,2,2-tetrahydrooctyl group or heptadecafluoro-1,1,2,2-tetrahydrooctyl group and at least one of R$^8$, R$^9$ and R$^{10}$ is the fluorine-containing substituent selected from the above substituents.

The seventh feature of the present invention is directed to a polyorganosiloxane compound of the above first to sixth features in which the substituent as represented by the reference symbol R$^2$ is:

$$-(CH_2)_3-(OCH_2CH_2)-OH$$

The eighth feature of the present invention is directed to a polyorganosiloxane compound of the above first to sixth features in which the substituent as represented by the reference symbol R$^2$ is:

$$-(CH_2)_3-OCH_2\underset{OH}{\overset{X^1}{C}}CH_2-OH$$

(wherein X$^1$ is a hydrogen atom, methyl group or ethyl group).

The nineth feature of the present invention is directed to a polyorganosiloxane compound of the above first to sixth features in which the substituent as represented by the reference symbol R$^2$ is:

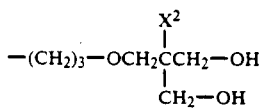

(wherein $X^2$ is a hydrogen atom, methyl group or ethyl group).

DESCRIPTION OF THE PREFERRED EMBODIMENTS

The polyorganosiloxane compounds according to the present invention have a hydroxyl group at its one terminal and a fluorine-containing substituent at the other terminal as is apparent from the general formulas (I), (VI) and (VII) of the first, third and fifth features.

This can be applied to the polyorganosiloxane having a larger molecular weight in which the reference symbol in the general formula (I), k and l in the general formula (VI), as well as m, n and p in the general formula (VII) become larger.

The polyorganosiloxane compounds according to the preferred present invention are further characterized by a degree of polydispersion, i.e., a ratio of a weight-average molecular weight to a number-average molecular weight, Mw/Mn, in the range from 1.1 to 1.2. In other words, they are said to be a polymer in which a distribution of its molecular weight is highly controlled.

As is apparent from the general formulas (I), (VI) and (VII), the respective reference symbols j, k, l, m, n and p each represents the number of dimethylsiloxane units of the linear polydimethylsiloxane compound, each of the reference symbols is in the range from 2 to 2,000 in order to ensure a manifestation of functional characteristics inherent in the polydimethylsiloxane compound when introduced into the synthetic resins as well as to faciliate an introduction thereof into the synthetic resin and to enable a ready synthesis. Each of the reference symbols j, k, l, m, n and p is preferably below approximately 700 although preferred conditions for introduction of the polyorganosiloxane compounds according to the present invention into the synthetic resins may vary with the kind of the synthetic resins, characteristics of the polymers and functions required for the synthetic resins.

In the general formula (II) in the first, third and fifth features according to the present invention, the fluoroalkyl group represented by the general formula:

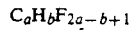

is such that the symbol a ranges generally from 3 to 18, preferably from 3 to 10, more preferably from 4 to 6. This range is preferred in terms of ready availability of raw materials, a ready synthesis, and an effective manifestation of functions inherent in the fluoroalkyl group, such as water or oil repellency, antifouling properties, mold releasability, non-adhesion, low frictional properties, snow resistance and the like.

The hydroxyl-containing substituents in the general formulas (III), (IV) and (V) according to the respective first, third and fifth features of the present invention are such that the symbol $h^0$ is in the range from 1 to 6 as well as the symbols $h^1$, $h^2$, $h^3$, $h^4$, $h^5$ and $h^6$ are each in the range from 0 to 20. The hydroxyl-containing substituents may be chosen depending upon ready availability of raw materials, compatibility with the synthetic resins, influences upon functions to be added, and ease of synthesis. As the numbers of the symbols $h^0$, $h^1$, $h^2$, $h^3$, $h^4$, $h^5$ and $h^6$ become larger, a compatibility with the synthetic resins is increased, yet other properties such as heat resistance may be adversely affected so that they should be preferably set in accordance with requirements for the characteristics being sought and the reason for addition of the polyorganosilloxane compound to the synthetic resins.

Although the polyorganosiloxane compounds according to the present invention may have two or three siloxane chains based on the hydrosilyl group as well as one siloxane chain based thereon, as are shown in the general formulas (VI), (V), and (I) in the respective third, fifth and first features of the present invention, they may be chosen depending upon the kinds of synthetic resins and functional characteristics to be added by introduction of the polyorganosiloxane compounds. When the polyorganosiloxane compounds having two or three siloxane chains based thereon are to be used as graft polymers for modifying the synthetic resins, it is preferred that the siloxane chains have the same length although the polyorganosiloxane compound with the plural siloxane chains of different length may be used in accordance with usage of the synthetic resins to which it is added. It is further to be noted that the substituents as represented by the symbols $R^5$ and $R^6$ of the general formula (VI) in the third feature and the symbols $R^8$, $R^9$ and $R^{10}$ of the general formula (VII) in the fifth feature according to the present invention, which are different from each other, may be introduced into the plural siloxane chains of the polyorganosiloxane compound. However, manufacture of the polyorganosiloxane compounds with the plural siloxane chains having different chain length and substituents is made complicated and conditions for synthesis become narrower, these compounds are not preferred unless a unique function is required to be added to the synthetic resin or a more sensitive control over functional characteristics to be added should be made. It is preferred that the siloxane chains are usually the same in chain length and substituents as each other.

The polyorganosiloxane compounds as represented by the general formula (I) in the first feature, the general formula (VI) in the third feature, and the general formula (VII) in the fifth feature of the present invention may be reacted with the synthetic resins obtainable by reaction of reactive hydroxyl groups such as polyurethane, polyester or the like which, in turn, are reactive with the hydroxyl group present at one terminal of the polyorganosiloxane compounds according to the present invention. A chemical introduction of the polyorganosiloxane compound into the synthetic resin through a chemical bond provides effective improvements in characteristics of the synthetic resins, particularly improvements in modifying a resin surface of the synthetic resins.

The polyorganosiloxane compounds represented by the general formulas (I), (VI) and (VII) may be prepared by the following procedures:

(1) The polyorganosiloxane compound having one siloxane chain based on the hydrosilyl group:
   The reaction scheme may be described as follows:

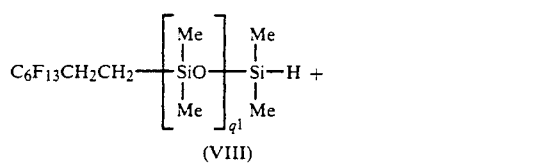

(VIII)

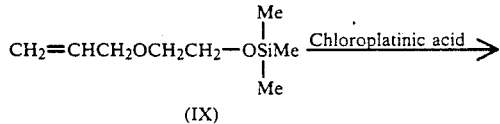

(IX)

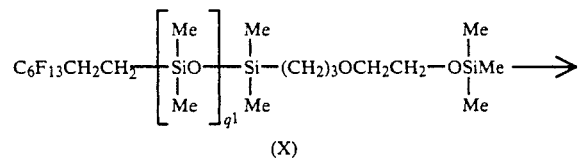

(X)

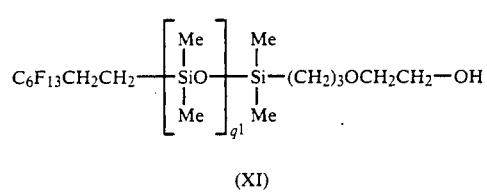

(XI)

(wherein Me is methyl and $q^1$ is an integer from 2 to 2,000).

Using (tridecafluoro-1,1,2,2-tetrahydrooctyl)dimethylsilanol as an initiator, hexamethylcyclotrisiloxane is first subjected to anionic polymerization in the presence of a lithium catalyst in a polar solvent having no active hydrogen. Dimethylchlorosilane is then added to terminate the polymerization, thereby yielding a dimethylsiloxane compound (VIII) having a tridecafluoro-1,1,2,2-tetrahydrooctyl group at an α-terminal and a hydrosilyl group at an ω-terminal. The dimethylsiloxane compound (VIII) is then hydrosilylated with 2-(2-propenyloxy)ethoxytrimethylsilane (IX) in the presence of a catalyst to give a siloxane compound (X). Thereafter, the trimethylsilyl group of the siloxane compound (X) is removed by means of a dilute hydrochloric acid or an alcohol such as methanol or ethanol yielding the object compound, an organosiloxane compound (XI).

(2) The polyorganosiloxane compound having two siloxane chains based on the hydrosilyl group:

The reaction scheme may be described as follows:

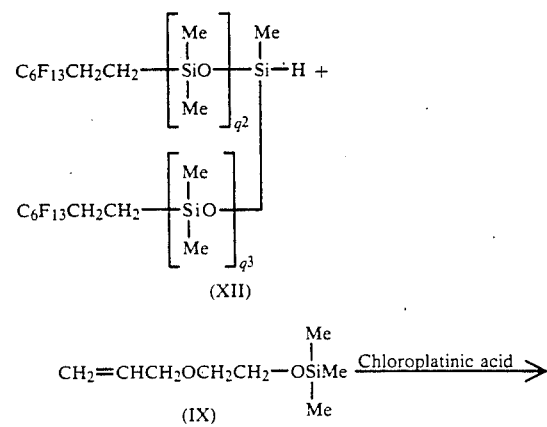

(XII)

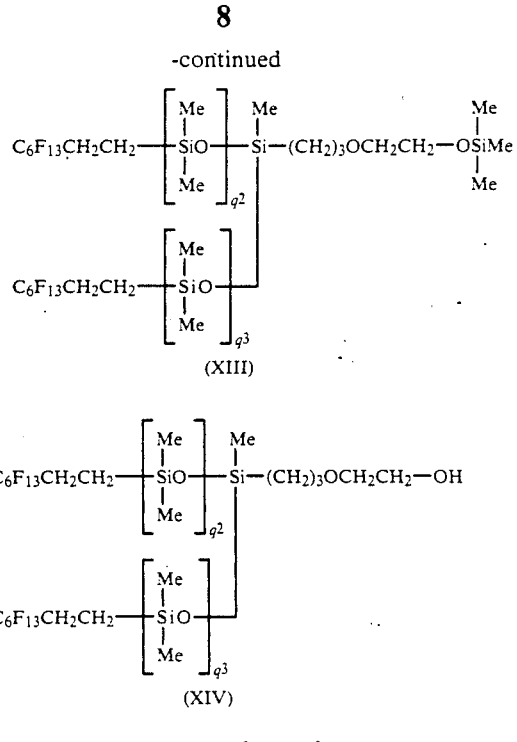

(XIII)

(XIV)

(wherein Me is methyl and $q^2$ and $q^3$ are independently each an integer from 2 to 2,000).

Using (tridecafluoro-1,1,2,2-tetrahydrooctyl)dimethylsilanol as an initiator, hexamethylcyclotrisiloxane is first subjected to anionic polymerization in the presence of a lithium catalyst in a polar solvent having no active hydrogen. Methyldichlorosilane is then added to terminate the polymerization, thereby yielding a dimethylsiloxane compound (XII) having a tridecafluoro-1,1,2,2-tetrahydrooctyl group at α- and α'-terminal positions and a hydrosilyl group at an ω-terminal position.

The dimethylsiloxane compound (XII) is then hydrosilylated with 2-(2-propenyloxy)ethoxytrimethylsilane (IX) in the presence of a catalyst to give a siloxane compound (XIII). Thereafter, the trimethylsilyl group of the siloxane compound (XIII) is removed by means of a dilute hydrochloric acid or an alcohol such as methanol or ethanol yielding the object compound, an organosiloxane compound (XIV).

(3) The polyorganosiloxane compound having three siloxane chains based on the hydrosilyl group:

The reaction scheme may be described as follows:

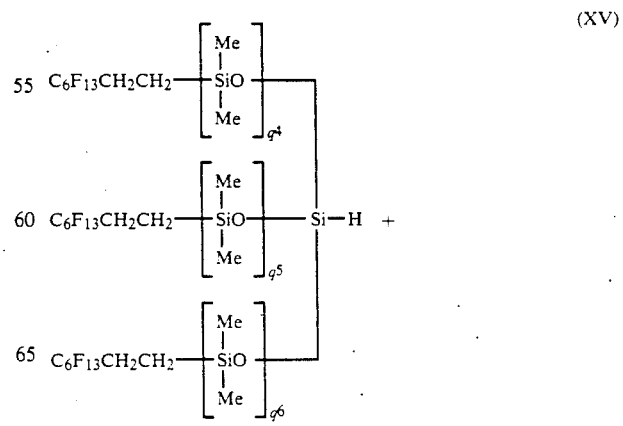

(XV)

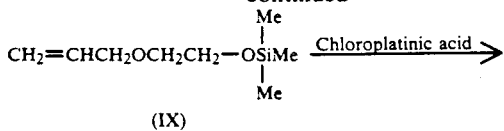

(IX)

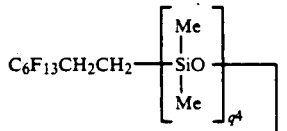

(XVI)

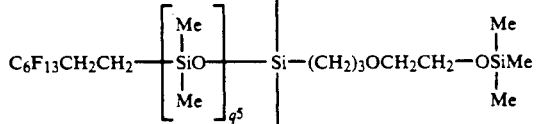

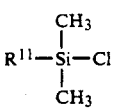

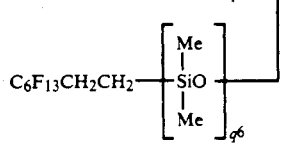

(XVII)

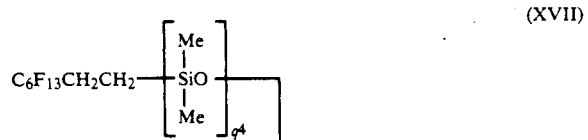

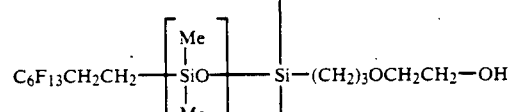

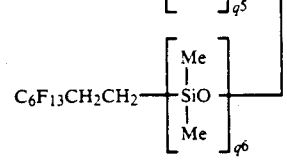

(wherein Me is methyl and $q^4$, $q^5$ and $q^6$ are independently each an integer from 2 to 2,000).

Using (tridecafluoro-1,1,2,2-tetrahydrooctyl)dimethylsilanol as an initiator, hexamethylcyclotrisiloxane is first subjected to anionic polymerization in the presence of a lithium catalyst in a polar solvent having no active hydrogen. Trichlorosilane is then added to terminate the polymerization, thereby yielding a dimethylsiloxane compound (XV) having a tridecafluoro-1,1,2,2-tetrahydrooctyl group at an α-, α'- and α''-terminal positions and a hydrosilyl group at an ω-terminal position.

The dimethylsiloxane compound (XV) is then hydrosilylated with 2-(2-propenyloxy)ethoxytrimethylsilane (IX) in the presence of a catalyst to give a siloxane compound (XVI). Thereafter, the trimethylsilyl group of the siloxane compound (XVI) is removed by means of a dilute hydrochloric acid or an alcohol such as methanol or ethanol yielding the object compound, an organosiloxane compound (XVII).

In preparing the polyorganosiloxane compounds according to the present invention having one, two or three siloxane chains based on the hydrosilyl group, a control over molecular weights and a distribution of the molecular weights is made by the siloxane compounds represented by the formulas (VIII), (XII), and (XV), respectively. The siloxane compounds with the objective molecular weights with a number-average molecular weight of approximately 150,000 or lower (2,000 or lower of siloxane units) per siloxane chain may be synthesized without difficulty by changing a ratio of an initiator such as a trialkylsilanol, i.e., (tridecafluoro-1,1,2,2-tetrahydrooctyl)dimethylsilanol, to hexamethylcyclotrisiloxane. The siloxane compounds having a molecular weight larger than the above molecular weight may be prepared by changing polymerization conditions.

The trialkylsilanol to be used as an initiator for the anionic polymerization may be readily available by hydrolyzing a trialkylchlorosilane having the objective alkyl group. The trialkylchlorosilane may be represented by the following general formula:

$$R^{11}-\underset{\underset{CH_3}{|}}{\overset{\overset{CH_3}{|}}{Si}}-Cl$$

wherein $R^{11}$ is pentafluorophenyl group or a linear or branched fluoroalkyl alkyl group as represented by the above-mentioned general formula (II), when the organosiloxane compound as represented by the formula (I) above is prepared, or an alkyl group having 1 to 4 carbon atoms, a phenyl group, pentafluorophenyl group or a linear or branched fluoroalkyl group as represented by the general formula (II) above when the organosiloxane compound as represented by the general formula (VI) or (VII) above is prepared.

The trialkylchlorosilane as represented by the general formula above may include, for example, trimethylchlorosilane, ethyldimethylchlorosilane, n-butyldimethylchlorosilane, t-butyldimethylchlorosilane, isopropyldimethylchlorosilane, n-propyldimethylchlorosilane, pentafluorophenyldimethylchlorosilane, 3,3,3-trifluoropropyldimethylchlorosilane, (tridecafluoro-1,1,2,2-tetrahydrooctyl)dimethylchlorosilane, (heptadecafluoro-1,1,2,2-tetrahydrodecyl)dimethylchlorosilane or the like.

The lithium catalyst to be used for synthesis of the compound according to the present invention may include, for example, a metal lithium, butyl lithium, lithium hydroxide or a lithium trialkylsilanolate as represented by following general formula:

$$R^{11}-\underset{\underset{CH_3}{|}}{\overset{\overset{CH_3}{|}}{Si}}-OLi$$

(where $R^{11}$ has the same meaning as above). The lithium catalyst may be used singly or in combination thereof. It is further to be noted that, for example, a sodium catalyst, potassium catalyst or other alkali metal catalyst may be employed, however, it is not preferred because a yield of the siloxane compound may be reduced.

The amount of the catalyst for the anionic polymerization may be in the range generally from 0.05 mol % to 50 mol %, preferably from 0.05 mol % to 10 mol %, with respect to the amount of the trialkylsilanol as a polymerization initiator. If the catalyst is used in an amount below the lower limit, the polymerization speed becomes too slow to be practical. It is preferred to use the catalyst in the amount up 50 mol %, generally up 10 mol %, if metering would become inaccurate on account of too small an amount in the case where the synthesis scale is too small or a polymer with a high molecular weight is synthesized. Even if the catalyst is used in amounts from 50 mol % to 100 mol %, synthesis proceeds without difficulty, however, the use of the catalyst in such a large amount is not preferred because security may be impaired, production efficiency may be reduced, and a production cost may be raised due to the use of a dangerous and expensive catalyst, unless a special circumstance would arise.

The polar solvent having no active hydrogen to be used for synthesis of the polyorganosiloxane compounds may include, for example, tetrahydrofuran, 1,4-dioxane, ethyleneglycol dimethylether, diethyleneglycol dimethylether, dimethylformamide, dimethylsulfoxide or the like. Preferred is tetrahydrofuran although the solvent may be used in combination thereof. A solvent with an active hydrogen interferes with the reaction and a non-polar solvent results in the reaction proceeding too slowly so that these solvents cannot be used.

Reaction temperatures may be in the range generally from 0° C. to 50° C., preferably from 15° C. to 25° C. If the reaction temperature becomes too low, a polymerization speed becomes too slow to be practical, while a reaction temperature above the upper limit is not preferred because it causes a polysiloxane compound to have too wide a molecular weight distribution.

Reaction time may vary with reaction temperatures and it is preferred to determine the reaction time so as to suspend the reaction at the time when hexamethylcyclotrisiloxane used is consumed by approximately 95%. For example, a period of time ranging from 10 to 20 hours is appropriate in the case of reaction temperatures ranging from 15° C. to 20° C. A reaction time longer than necessary is not preferred because it broadens the molecular weight distribution too much.

2-(2-Propenyloxy)ethoxytrimethylsilane as represented by formula (IX) above, in which the hydroxyl group at its terminal of 2-(2-propenyloxy)ethanol is protected with a trimethylsilyl group, may be readily prepared by reacting 2-(2-propenyloxy)ethanol with hexamethyldisilazane in the presence of trimethylchlorosilane.

For the hydrosilylation, a catalyst to be used may be a complex compound of a metallic element of Group VIII of the Periodic Table, including preferably chloroplatinic acid or a complex of platinum or rhodium with an olefin. An amount of chloroplatinic acid as a catalyst may be in the range preferably from $1 \times 10^{-3}$ to $1 \times 10^{-6}$ mol per mol of the siloxane compound as represented by the general formula (VIII), (XII) or (XV). If the catalyst is used above the upper limit, it may incur the increasing possibility of breaking the siloxane chain and raise the cost of production due to the use of the catalyst in too great an amount. If the amount of the catalyst is below the lower limit, the reaction becomes likely to undergo influences from a minute amount of moisture or substances detrimental to the reaction so that the reaction may not proceed in a smooth manner.

The reaction temperature may be in the range preferably from 50° C. to 150° C., more preferably from 80° C. to 120° C. A reaction temperature below the lower limit may pose the problems that the reaction does not proceed smoothly or the reaction period becomes too long. If the reaction temperature would exceed the upper limit, it is not preferred that a siloxane chain may be broken or a side reaction may arise upon removal of the trimethylsilyl group from the protective site of an olefin such as 2-(2-propenyloxy)ethoxytrimethylsilane or the like.

In preparing the siloxane compounds according to the present invention, having one, two or three siloxane chains based on the hydrosilyl group, it is further to be noted that, in place of 2-(2-propenyloxy)ethoxytrimethylsilane as represented by formula (IX), a siloxane compound having two primary and secondary hydroxyl groups, which differ in reactivity from each other, at its terminal may be prepared using 1,2-bis(-trimethylsiloxy)-3-allyloxypropane as represented by formula (XVIII) below or 1-trimethysiloxy- 3-allyloxypropan-2-ol as represented by formula (XVIII'),each being obtainable by reacting 3-allyloxypropane-1,2-diol in the presence of hexamethyldisilazane and trimethylchlorosilane:

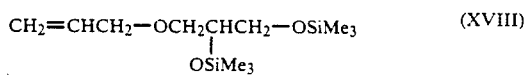

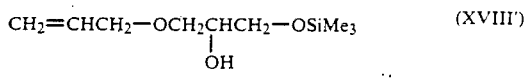

(where Me is methyl).

It is also to be noted that a siloxane compound having two primary hydroxyl groups at its terminal may be prepared using 1,3-bis(trimethylsiloxy)-2-(2-propenyloxy) -methyl-2-alkylpropane as represented by formula (XIX) obtainable by reaction of 2-(2-propenyloxy)methyl-2-alkYlpropane-1,3-diol in the presence of hexamethyldisilazane and trimethylchlorosilane:

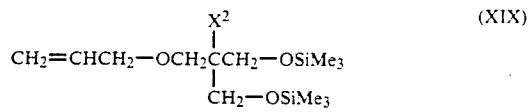

(Where Me is methyl and $X^2$ is a hydrogen atom, methyl or ethyl).

The length of an alkylene oxide site of the hydroxyl-containing substituent may be adjusted by means of a conventional synthesis of polyalkylene oxides ("Yukagaku"; vol.31, No.5 (1982), pp. 253–261).

In a similar manner as above, the polyorganosiloxne compounds according to the present invention can be obtained, which compounds have a fluorine-containing group at its α-position and one or more than one hydrosilyl group at its ω-position, have a fluorine-containing group at least at its α- and α'- position and one or more than one hydrosilyl group at its ω-position or which has a fluorine-containing group at least at its α-, α'- and α"-position and one or more than one hYdrosilYl group at its ω-position.

The present invention will be described more in detail by way of examples.

Reference Example 1

Preparation of 1-(tridecafluoro-1,1,2,2-tetrahydrooctyl)-9-hydrodecamethyl pentasiloxane A 1-liter three-necked round flask with a stirrer and a cooler was charged with 100 ml of previously dried tetrahydrofuran, 100.0 g (0.238 mol) of (tridecafluoro-1,1,2,2-tetrahydrooctyl)dimethylsilanol, and 52.9 g (0.238 mol) of hexamethylcyclotrisiloxane in a nitrogen stream, and 0.79 ml of a hexane solution of butyl lithium (1.5 mol/liter) was added to the mixture. The polymerization was then carried out at 20° C. for 10 hours.

To the reaction mixture were then added 24.7 g (0.261 mol) of dimethylchlorosilane and 27 g of triethyl amine, and the mixture was stirred for 1 hour to suspend the polymerization. The product was then transferred to a separatory funnel and the salt produced was removed by washing with water. The product was then dried over anhydrous sodium sulfate.

A low-boiling fraction of the reaction product was removed at 100° C./100 mmHg over a period of 2 hours and the object product was left as a still residue in a substantially quantitative yield. The resulting siloxane compound was measured by $^1$H-NMR spectrum, IR spectrum, and gel permeation chromatography (GPC) and the analysis results and Si—H group quantitation data are as shown below. The resulting product was identified as having the following formula:

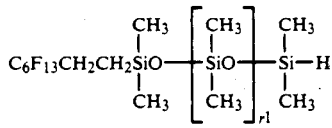

$^1$H-NMR (CDCl$_3$): δ ppm.
0.18 (Si (C$\underline{H}_3$)$_2$, s, 30H),
0.53~1.80 (SiC$\underline{H}_2$C$\underline{H}_2$, broad, 4H),
4.55 (Si—$\underline{H}$, m, 1H)
IR (KBr):
2,970 cm$^{-1}$ (C—H),
2,250 cm$^{-1}$ (Si—H),
1,260 cm$^{-1}$ (SI—CH$_3$),
1,250~1,150 cm$^{-1}$ (CF$_2$, CF$_3$),
1,120~1,050 cm$^{-1}$ (SI—O)

| GPC (toluene), molecular weight converted into polystyrene | |
|---|---|
| number-average molecular weight (Mn) | 850 |
| weight-average molecular weight (Mw) | 930 |
| polydispersion degree (Mw/Mn) | 1.1 |
| calculated molecular weight, | 702) |
| Quantitation Data of Si—H group: | |
| H (ppm) | 1442 (ppm) |
| Molecular weight calculated from H(ppm): | 693 | r$^1$ in the present example and r$^2$-r$^8$ in subsequent examples may be calculated based on the following general formula and equation:

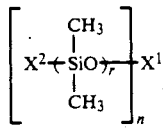

where
X$^2$=Substituent containing fluorine
X$^1$=Substituent containing OH
r=Number of units
n=1 to 3 (n=1 in the present example)

$$r=[\{(a-b)/n\}-c]/d$$

where
a=Calculated molecular weight from quantitation data
b=Calculated molecular weight of X$^2$
c=Calculated molecular weight of X$^1$
d=Calculated molecular weight of —Si(CH$_3$)$_2$—

Example 1

Preparation of 1-(tridecafluoro-1,1,2,2-tetrahydrooctyl)-9-[3-(2-hydroxylethoxy)propyl]decamethylpentasiloxane A 1-liter three-necked round flask with a stirrer and a cooler was charged with 69.3 g of 1-(tridecafluoro-1,1,2,2-tetrahydrooctyl)-9-hydrodecamethylpentasiloxane prepared in Reference Example 1 above and heated to 100° C. After 5.2×10$^{-4}$ g (1.0×10$^{-6}$ mol) of chloroplatinic acid was added, 19.1 g (0.11 mol) of 2-(2-propenyloxy)ethoxytrimethylsilane was dropwise added. After completion of dropwise addition, the mixture was maintained at the reaction temperature of 100° C. for 5 hours and then subjected to a reaction for removing a trimethylsilyl group using 70 g of methanol.

A low-boiling fraction of the reaction product was removed at 100° C./100 mmHg over a period of 2 hours and the object product was left as a still residue in a substantially quantitative yield. The resulting siloxane compound was measured by $^1$H-NMR spectrum, IR spectrum, gel permeation chromatography (GPC) and viscosity, and the analysis results and hydroxy group quantitation data are as shown below. The resulting product was identified as having the following formula:

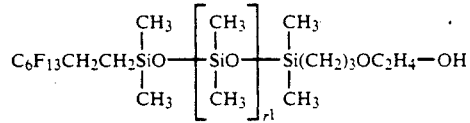

$^1$H-NMR (CDCl$_3$): δ ppm:
0.18 (Si(C$\underline{H}_3$)$_2$, s, 30H),
0.53~1.80 (SiC$\underline{H}_2$C$\underline{H}_2$—, broad, 8H),
3.30~3.70 (—C$\underline{H}_2$O—, broad, 6H)
IR (KBr):
3,650—3,200 cm$^{-1}$ (—OH),
2,970 cm$^{-1}$ (C—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 930 |
| weight-average molecular weight (Mw) | 1,020 |
| polydispersion degree (Mw/Mn) | 1.1 |
| calculated molecular weight, | 803) |
| Quantitation Data of OH group: | |
| OH (% by weight) | 2.0 |
| calculated molecular weight from OH (% by weight) | 850 |
| Viscosity (25° C.): | 18 centipoises |

Reference Example 2

Preparation of dimethylsiloxan compound having a tridecafluoro-1,1,2,2-tetrahydrooctyl group at its α-position and a hydrosilyl group at its ω-position A 2-liter three-necked round flask with a stirrer and a cooler was charged with 400 ml of previously dried tetrahydrofuran, 5.0 g (0.0119 mol) of (tridecafluoro-1,1,2,2-tetrahydrooctyl)dimethylsilanol, and 350.5 g (1.57 mol) of hexamethylcyclotrisiloxane in a N$_2$ stream. After addition of 0.040 ml of a hexane solution of butyl lithium (1.5 mol/liter), the polymerization was carried out at 20° C. for 15 hours.

To the reaction mixture were added 1.24 g (0.0131 mol) of dimethylchlorosilane and 2 g of triethylamine, and the mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (SI—CH$_3$),
1,250~1,150 cm$^{-1}$ (CF$_2$, CF$_3$),
1,120~1,050 cm$^{-1}$ (SI—O)

| GPC (toluene), molecular weight converted into polystyrene | |
|---|---|
| number-average molecular weight (Mn) | 32,660 |
| weight-average molecular weight (Mw) | 35,930 |
| polydispersion degree (Mw/Mn) | 1.1 |
| Quantitation Data of Si—H group: | |
| H (ppm) | 32.1 |
| calculated molecular weight from H (ppm) | 31,153 |
| Viscosity (25° C.): | 1,385 centipoises |

Example 2

Preparation of dimethylsiloxane compound having a tridecafluoro-1,1,2,2-tetrahydrooctyl group at its α-position and a 3-(3-hydroxy-2-ethyl-2-methanolpropoxy)propyl group at its ω-position A 2-liter three-necked round flask with a stirrer and a cooler was charged with 311.5 g of the siloxane compound prepared in Reference Example 2 and 100 ml of toluene and heated to 100° C. After 5.2×10$^{-5}$ g (1.0×10$^{-7}$ mol) of chloroplatinic acid was added to the mixture, 3.5 g (0.011 mol) of 1,3-bis(trimethylsiloxane)-2-(2-propenyloxy)methyl-2-ethylpropane was dropwise added. After the completion of dropwise addition, the reaction mixture was maintained at 100° C. for 20 hours and then subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and OH group quantitation data are as shown below.

IR (KBr):
3,650~3,200 cm$^{-1}$ (—OH),
2,970 cm$^{-1}$ (C—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 32,600 |
| weight-average molecular weight (Mw) | 37,700 |
| polydispersion degree (Mw/Mn) | 1.2 |
| Quantitation Data of OH group: | |
| OH (% by weight) | 0.11 |
| calculated molecular weight from OH (% by weight) | 31,000 |
| Viscosity (25° C.): | 1,424 centipoises |

Reference Example 3

Preparation of dimethylsiloxane compound with a tridecafluoro-1,1,2,2-tetrahydrooctyl group at its α-position and a hydrosilyl group at its ω-position A 5-liter three-necked round flask with a stirrer and a cooler was charged with 2,000 ml of previously dried tetrahydrofuran, 12.0 g (0.0285 mol) of (tridecafluoro-1,1,2,2-tetrahydrooctyl)dimethylsilanol, and 1,981.1 g (8.90 mol) of hexamethylcyclotrisiloxane in a N$_2$ stream. To this mixture was added 0.095 ml of a hexane solution of butyl lithium (1.5 mol/liter), and the mixture was subjected to polymerization at 20° C. for 20 hours.

To this reaction mixture were then added 2.97 g (0.0313 mol) of dimethylchlorosilane and 3.17 g of triethylamine, and the mixture was stirred for 1 hour to suspend the polymerization. After the reaction mixture was transferred to a separatory funnel and the salt produced was removed by washing with water, the reaction product was dried over anhydrous sodium sulfate.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 63,410 |
| weight-average molecular weight (Mw) | 75,930 |
| polydispersion degree (Mw/Mn) | 1.2 |
| Quantitation Data of Si—H group: | |
| H (ppm) | 15.1 |
| calculated molecular weight from H (ppm) | 66,225 |
| Viscosity (25° C.) | 3,538 centipoises |

Example 3

Preparation of dimethylsiloxane compound with a tridecafluoro-1,1,2,2-tetrahydrooctyl group at its α-position and a 3-(2,3-dihydroxypropoxy)propyl group at its ω-position A 3-liter three-necked round flask with a stirrer and a cooler was charged with 662.2 g of the siloxane compound prepared in Reference Example 3 and 500 ml of toluene and heated to 100° C. After addition of 5.2×10$^{-5}$ g (1.0×10$^{-7}$ mol) of chloroplatinic acid, 2.25 g (0.011 mol) of 1-trimethylsiloxy-3-allyloxypropan-2-ol was dropwise added. After the completion of dropwise addition, the reaction mixture was maintained at the reaction temperature of 100° C. for 20 hours and subjected to a reaction for removing its trimethylsilyl group using 300 g of methanol.

A low-boiling fraction of the reaction product was removed off at 100° C./10 mmHg over a period of 2 hours and the object product was left as a still residue in a substantially quantitative Yield. The resulting siloxane compound was measured by IR spectrum, gel permeation chromatography (GPC) and viscosity, and the analysis results and OH group quantitation data are as shown below.

IR (KBr):
3,650~3,200 cm$^{-1}$ (—H),
2,970 cm$^{-1}$ (C—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 65,100 |
| weight-average molecular weight (Mw) | 78,100 |
| polydispersion degree (Mw/Mn) | 1.2 |
| Quantitation Data of OH group: | |
| OH (% by weight) | 0.051 |
| calculated molecular weight from OH (% by weight) | 66,700 |
| Viscosity (25° C.): | 3,890 centipoises |

Reference Example 4

Preparation of dimethylsiloxane compound with a heptadecafluoro-1,1,2,2-tetrahydrodecyl group at its α-position and a hydrosilyl group at its ω-position A 5-liter three-necked round flask with a stirrer and a cooler was charged with 2,000 ml of previously dried tetrahydrofuran, 100.0 g (0.1915 mol) of (heptadecafluoro-1,1,2,2-tetrahydrodecyl)dimethylsilanol, and 1,803.6 g (8.10 mol) of hexamethylcyclotrisiloxane in a N$_2$ stream. After 0.64 ml of a hexane solution of butyl lithium (1.5 mol/liter) was added, the mixture was polYmerized at 20° C. for 15 hours.

To this reaction mixture were added 19.9 g (0.211 mol) of dimethylchlorosilane and 21.4 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C. /10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 11,710 |
| weight-average molecular weight (Mw) | 12,896 |
| polydispersion degree (Mw/Mn) | 1.1 |
| Quantitation Data of Si—H group: | |
| H (ppm) | 103.3 |
| calculated molecular weight from H (ppm) | 9,680 |
| Viscosity (25° C.): | 147 centipoises |

Example 4

Preparation of dimethylsiloxane compound with a heptadecafluoro-1,1,2,2-tetrahydrodecyl group at its α-position and a 3-(2-hydroxylethoxy)propyl group at its ω-position A 3-liter three-necked round flask with a stirrer and a cooler was charged with 968.0 g of the siloxane compound prepared in Reference Example 4 and 400 ml of toluene and heated to 100° C. After addition of 5.2×10$^{-4}$ g (1.0×10$^{-6}$ mol) of chloroplatinic acid, 14.4 g (0.11 mol) of 2-(2-propenyloxy)trimethylsilane was dropwise added. After the completion of dropwise addition, the reaction mixture was maintained at the reaction temperature of 100° C. for 20 hours and subjected to a reaction for removing its trimethylsilyl group using 500 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and OH group quantitation data are as shown below.

IR (KBr):
3,650~3,200 cm$^{-1}$ (—OH),
2,970 cm$^{-1}$ (C—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 11,840 |
| weight-average molecular weight (Mw) | 13,020 |
| polydispersion degree (Mw/Mn) | 1.1 |
| Quantitation Data of OH group: | |
| OH (% by weight) | 0.17 |
| calculated molecular weight from OH (% by weight) | 10,000 |
| Viscosity (25° C.): | 179 centipoises |

Reference Example 5

Preparation of dimethylsiloxane compound with a 3,3,3-trifluoropropyl group at its α-position and a hydrosilyl group at its ω-position A 2-liter three-necked round flask with a stirrer and a cooler was charged with 800 ml of previously dried tetrahydrofuran, 10.0 g (0.0581 mol) of (3,3,3-trifluoropropyl)dimethylsilanol, and 567.2 g (2.55 mol) of hexamethylcyclotrisiloxane in a N$_2$ stream. After 0.19 ml of a hexane solution of butyl lithium (1.5 mol/liter) was added, the mixture was polYmerized at 20° C. for 15 hours.

To this reaction mixture were added 6.04 g (0.0639 mol) of dimethylchlorosilane and 6.5 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative Yield. The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 9,520 |
| weight-average molecular weight (Mw) | 10,490 |
| polydispersion degree (Mw/Mn) | 1.1 |
| Quantitation Data of Si—H group: | |
| H (ppm) | 112.5 |
| calculated molecular weight from H (ppm) | 8,890 |
| Viscosity (25° C.): | 116 centipoises |

Example 5

Preparation of dimethylsiloxane compound with a 3,3,3-trifluoropropyl group at its α-position and a 3-(2-hydroxylethoxy)propyl group at its ω-position A 1-liter three-necked round flask with a stirrer and a cooler was charged with 88.9 g of the siloxane compound prepared in Reference Example 5 and 50 ml of toluene and heated to 100° C. After addition of 5.2×10$^{-5}$ g (1.0×10$^{-7}$ mol) of chloroplatinic acid, 1.91 g (0.011 mol) of 2-(2-propenyloxy)ethoxytrimethylsilane was dropwise added. After the completion of dropwise addition, the reaction mixture was maintained at the reaction temperature of 100° C. for 20 hours and subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and OH group quantitation data are as shown below.

IR (KBr):
3,650~3,200 cm$^{-1}$ (—OH),
2,970 cm$^{-1}$ (C—H),
1,260 cm$^{-1}$ (Si—CH$_3$),
1,250~1,150 cm$^{-1}$ (CF$_2$, CF$_3$),
1,120~1,050 cm$^{-1}$ (Si—O)

| GPC (toluene), molecular weight converted into polystyrene | |
|---|---|
| number-average molecular weight (Mn) | 11,700 |
| weight-average molecular weight (Mw) | 12,800 |
| polydispersion degree (Mw/Mn) | 1.1 |
| Quantitation Data of OH group: | |
| OH (% by weight) | 0.18 |
| calculated molecular weight from OH (% by weight) | 9,400 |
| Viscosity (25° C.): | 167 centipoises |

Reference Example 6

Preparation of dimethylsiloxane compound with a pentafluorophenyl group at its α-position and a hydrosilyl group at its ω-position A 1-liter three-necked round flask with a stirrer and a cooler was charged with 100 ml of previously dried tetrahydrofuran, 10.0 g (0.04127 mol) of pentafluorophenyldimethylsilanol, and 194.0 g (0.138 mol) of hexamethylcyclotrisiloxane in a N$_2$ stream. After 0.14 ml of a hexane solution of butyl lithium (1.5 mol/liter) was added, the mixture was polymerized at 20° C. for 15 hours.

To this reaction mixture were added 4.29 g (0.0454 mol) of dimethylchlorosilane and 4.6 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./100 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,120~1,050 cm$^{-1}$ (Si—O)

| GPC (toluene), molecular weight converted into polystyrene | |
|---|---|
| number-average molecular weight (Mn) | 5,807 |
| weight-average molecular weight (Mw) | 6,370 |
| polydispersion degree (Mw/Mn) | 1.1 |
| Quantitation Data of Si—H group: | 203.3 |
| H (ppm) | |
| calculated molecular weight from H (ppm) | 4,920 |
| Viscosity (25° C.): | 64 centipoises |

Example 6

Preparation of dimethylsiloxane compound with a pentafluorophenyl group at its α-position and a 3-(2-hydroxylethoxy)propyl group at its ω-position A 1-liter three-necked round flask with a stirrer and a cooler was charged with 49.2 g of the siloxane compound prepared in Reference Example 6 and 50 ml of toluene and heated to 100° C. After addition of 5.2×10$^{-5}$ g (1.0×10$^{-7}$ mol) of chloroplatinic acid, 1.31 g (0.011 mol) of 2-(2-propenyloxy)ethoxytrimethylsilane was dropwise added. After the completion of dropwise addition, the reaction mixture was maintained at the reaction temperature of 100° C. for 20 hours and subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and OH group quantitation data are as shown below.

IR (KBr):
3,650–3,200 cm$^{-1}$ (—OH),
2,970 cm$^{-1}$ (C—H),
1,260 cm$^{-1}$ (Si—CH$_3$),
1,250–1,150 cm$^{-1}$ (CF$_2$, CF$_3$),
1,120–1,050 cm$^{-1}$ (Si—O)

| GPC (toluene), molecular weight converted into polystyrene | |
|---|---|
| number-average molecular weight (Mn) | 5,300 |
| weight-average molecular weight (Mw) | 6,310 |
| polydispersion degree (Mw/Mn) | 1.2 |
| Quantitation Data of OH group: OH (% by weight) | 0.33 |
| calculated molecular weight from OH (% by weight) | 5,150 |
| Viscosity (25° C.): | 86 centipoises |

Reference Example 7

Preparation of dimethylsiloxane compound with a tridecafluoro-1,1,2,2-tetrahydrooctylphenyl group at its α-position and a hydrosilyl group at its ω-position A 5-liter three-necked round flask with a stirrer and a cooler was charged with 1,000 ml of previously dried tetrahydrofuran, 50.0 g (0.119 mol) of (tridecafluoro-1,1,2,2-tetrahydrooctyl)dimethylsilanol, and 1,130.2 g (5.08 mol) of hexamethylcyclotrisiloxane in a N$_2$ stream. After 0.40 ml of a hexane solution of butyl lithium (1.5 mol/liter) was added, the mixture was polymerized at 20° C. for 15 hours.

To this reaction mixture were added 12.35 g (0.1306 mol) of dimethylchlorosilane and 14 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,250–1,150 cm$^{-1}$ (CF$_2$, CF$_3$),
1,120–1,050 cm$^{-1}$ (Si—O)

| GPC (toluene), molecular weight converted into polystyrene | |
|---|---|
| number-average molecular weight (Mn) | 11,910 |
| weight-average molecular weight (Mw) | 12,850 |
| polydispersion degree (Mw/Mn) | 1.1 |
| Quantitation Data of Si—H group: H (ppm) | 101.6 |
| calculated molecular weight from H (ppm) | 9,843 |
| Viscosity (25° C.): | 165 centipoises |

Example 7

Preparation of dimethylsiloxane compound with a tridecafluoro-1,1,2,2-tetrahydrooctyl group at its α-position and a 3-(2-hydroxylethoxy)propyl group at its ω-position A 3-liter three-necked round flask with a stirrer and a cooler was charged with 984.3 g of the siloxane compound prepared in Reference Example 7 and 400 ml of toluene and heated to 100° C. After 5.2×10$^{-4}$ g (1.0×10$^{-6}$ mol) of chloroplatinic acid was added, 19.1 g (0.11 mol) of 2-(2-propenyloxy)ethoxytrimethylsilane was dropwise added. After completion of dropwise addition, the mixture was maintained at the reaction temperature of 100° C. for 20 hours and then subjected to a reaction for removing a trimethylsilyl group using 500 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and hydroxy group quantitation data are as shown below.

The resulting product was identified as having the following formula:

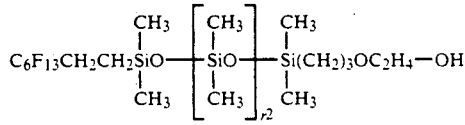

IR (KBr):
3,650–3,200 cm$^{-1}$ (—OH),
2,970 cm$^{-1}$ (C—H),
1,260 cm$^{-1}$ (Si—CH$_3$),
1,250–1,150 cm$^{-1}$ (CF$_2$, CF$_3$),
1,120–1,050 cm$^{-1}$ (Si—O)

| GPC (toluene), molecular weight converted into polystyrene | |
|---|---|
| number-average molecular weight (Mn) | 12,500 |
| weight-average molecular weight (Mw) | 13,700 |
| polydispersion degree (Mw/Mn) | 1.1 |
| Quantitation Data of OH group: OH (% by weight) | 0.17 |
| calculated molecular weight from OH (% by weight) | 10,000 |
| Viscosity (25° C.): | 204 centipoises |

Reference Example 8

Preparation of dimethylsiloxane compound (two siloxane chains based on the hydrosilyl group) with a tridecafluoro-1,1,2,2-tetrahydrooctyl group at its α- and α'-positions and a hydrosilyl group at its ω-position A 5-liter three-necked round flask with a stirrer and a cooler was charged with 1,000 ml of previously dried tetrahydrofuran, 50.0 g (0.119 mol) of (tridecafluoro-1,1,2,2-tetrahydrooctyl)dimethylsilanol, and 1,130.2 g (5.08 mol) of hexamethylcyclotrisiloxane in a N₂ stream. After 0.40 ml of a hexane solution of butyl lithium (1.5 mol/liter) was added, the mixture was polymerized at 20° C. for 15 hours.

To this reaction mixture were added 7.51 g (0.0653 mol) of methyldichlorosilane and 14 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below. It is further found that, as the molecular weights calculated from the GPC data and H (ppm) were virtually twice those of Reference Example 7 (having one siloxane chain based on the hydrosilyl group) in which the conditions and scales were the same as in this Reference Example yet only the kind of chlorosilane added was changed, the reaction product has the following structure having two siloxane chains as reference to the hydrosilyl group.

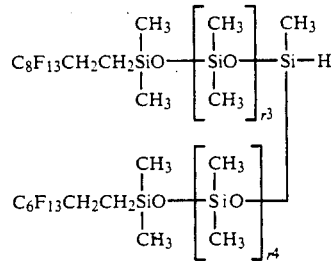

IR (KBr):
2,970 cm⁻¹ (C—H),
2,250 cm⁻¹ (Si—H),
1,260 cm⁻¹ (Si—CH₃),
1,250–1,150 cm⁻¹ (CF₂, CF₃),
1,120–1,050 cm⁻¹ (Si—O)

| GPC (toluene), molecular weight converted into polystyrene | |
|---|---|
| number-average molecular weight (Mn) | 19,740 |
| weight-average molecular weight (Mw) | 23,720 |
| polydispersion degree (Mw/Mn) | 1.2 |
| Quantitation Data of Si—H group: H (ppm) | 53.9 |
| calculated molecular weight from H (ppm) | 18,550 |
| Viscosity (25° C.): | 423 centipoises |

Example 8

Preparation of dimethylsiloxane with tridecafluoro-1,1,2,2-tetrahydrooctyl group at its α- and α'-positions and a 3-(2-hydroxylethoxy)propyl group at its ω-position A 3-liter three-necked round flask with a stirrer and a cooler was charged with 185.5 g of the siloxane compound prepared in Reference Example 8 and 100 ml of toluene and heated to 100° C. After $5.2 \times 10^{-5}$ g ($1.0 \times 10^{-7}$ mol) of chloroplatinic acid was added, 1.91 g (0.011 mol) of 2-(2-propenyloxy)ethoxytrimethylsilane was dropwise added. After completion of dropwise addition, the mixture was maintained at the reaction temperature of 100° C. for 20 hours and then subjected to a reaction for removing a trimethylsilyl group using 300 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and hydroxy group quantitation data are as shown below.

The resulting product was identified as having the following formula:

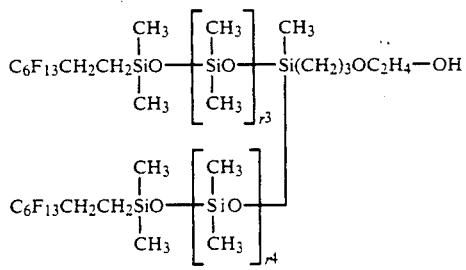

IR (KBr):
3,650–3,200 cm⁻¹ (—OH),
2,970 cm⁻¹ (C—H),
1,260 cm⁻¹ (Si—CH₃),
1,250–1,150 cm⁻¹ (CF₂, CF₃),
1,120–1,050 cm⁻¹ (Si—O)

| GPC (toluene), molecular weight converted into polystyrene | |
|---|---|
| number-average molecular weight (Mn) | 22,360 |
| weight-average molecular weight (Mw) | 24,600 |
| polydispersion degree (Mw/Mn) | 1.1 |
| Quantitation Data of OH group: OH (% by weight) | 0.086 |
| calculated molecular weight from OH (% by weight) | 19,800 |
| Viscosity (25° C.): | 482 centipoises |

Reference Example 9

Preparation of dimethylsiloxane compound (three siloxane chains based on the hydrosilyl group) with a tridecafluoro-1,1,2,2-tetrahydrooctyl group at its α-, α'- and α"-positions and a hydrosilyl group at its ω-position A 5-liter three-necked round flask with a stirrer and a cooler was charged with 1,000 ml of previously dried tetrahydrofuran, 50.0 g (0.119 mol) of (tridecafluoro-1,1,2,2-tetrahydrooctyl)dimethylsilanol, and 1,130.2 g (5.08 mol) of hexamethylcyclotrisiloxane in a N₂ stream. After 0.40 ml of a hexane solution of butyl lithium (1.5 mol/liter) was added, the mixture was polymerized at 20° C. for 15 hours.

To this reaction mixture were added 5.90 g (0.0453 mol) of trichlorosilane and 14 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below. It is further found that, as the molecular weights calculated from the GPC data and H (ppm) were virtually three times those of Reference Example 7 (having one siloxone chain based on the hydrosilyl group) in which the conditions and scales were the same as in Reference Example yet only the kind of chlorosilane added was changed, the reaction product has the following structure having three siloxane chains as reference to the hydrosilyl group.

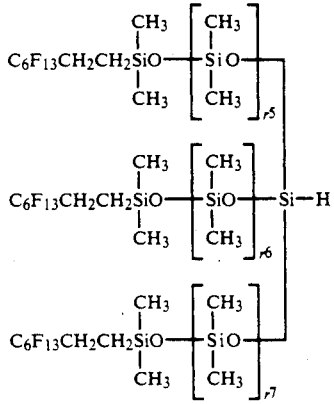

IR (KBr):
2,970 cm$^{-1}$ (C—H),
2,250 cm$^{-1}$ (Si—H),
1,260 cm$^{-1}$ (Si—CH$_3$),
1,250-1,150 cm$^{-1}$ (CF$_2$, CF$_3$),
1,120-1,050 cm$^{-1}$ (Si—O)

| GPC (toluene), molecular weight converted into polystyrene | |
|---|---|
| number-average molecular weight (Mn) | 33,790 |
| weight-average molecular weight (Mw) | 37,710 |
| polydispersion degree (Mw/Mn) | 1.1 |
| Quantitation Data of Si—H group: H (ppm) | 33.8 |
| calculated molecular weight from H (ppm) | 29,590 |
| Viscosity (25° C.): | 681 centipoises |

Example 9

Preparation of dimethylsiloxane compound with a tridecafluoro-1,1,2,2-tetrahydrooctyl group at its α-, α'- and α''-positions and a 3-(2-hydroxylethoxy)propyl group at its ω-position A 2-liter three-necked round flask with a stirrer and a cooler was charged with 295.9 g of the siloxane compound prepared in Reference Example 9 and 100 ml of toluene and heated to 100° C. After 5.2×10$^{-5}$ g (1.0×10$^{-7}$ mol) of chloroplatinic acid was added, 1.91 g (0.011 mol) of 2-(2-propenyloxy)ethoxytrimethylsilane was dropwise added. After completion of dropwise addition, the mixture was maintained at the reaction temperature of 100° C. for 20 hours and then subjected to a reaction for removing a trimethylsilyl group using 300 g of methanol.

A low-boiling fraction of the reaction product was removed at 100° C. /100 mmHg over a period of 2 hours and the object product was left as a still residue in a substantially quantitative yield.

The resulting siloxane compound was measured by IR spectrum, gel permeation chromatography (GPC) and viscosity, and the analysis results and hydroxy group quantitation data are as shown below.

The resulting product was identified as having the following formula:

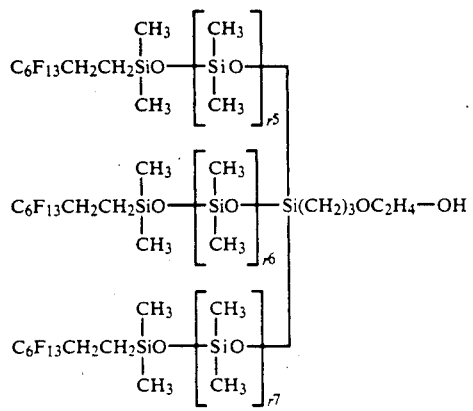

IR (KBr):
3,650-3,200 cm$^{-1}$ (—OH),
2,970 cm$^{-1}$ (C—H),
1,260 cm$^{-1}$ (Si—CH$_3$),
1,250-1,150 cm$^{-1}$ (CF$_2$, CF$_3$),
1,120-1,050 cm$^{-1}$ (Si—O)

| GPC (toluene), molecular weight converted into polystyrene | |
|---|---|
| number-average molecular weight (Mn) | 31,800 |
| weight-average molecular weight (Mw) | 38,120 |
| polydispersion degree (Mw/Mn) | 1.2 |
| Quantitation Data of OH group: OH (% by weight) | 0.057 |
| calculated molecular weight from OH (% by weight) | 29,800 |
| Viscosity (25° C.): | 753 centipoises |

Reference Example 10

Preparation of dimethylsiloxane compound with a tridecafluoro-1,1,2,2-tetrahydrooctyl group at its α-position and a hydrosilyl group at its ω-position A 3-liter three-necked round flask with a stirrer and a cooler was charged with 500 ml of previously dried tetrahydrofuran, 25.0 g (0.060 mol) of (tridecafluoro-1,1,2,2-tetrahydrooctyl)dimethylsilanol, and 565.1 g (2.54 mol) of hexamethylcyclotrisiloxane in a N$_2$ stream. After 0.20 ml of a hexane solution of butyl lithium (1.5 mol/liter) was added, the mixture was polymerized at 20° C. for 15 hours.

To this reaction mixture were added 6.17 g (0.065 mol) of dimethylchlorosilane and 7 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below.

IR (KBr):
2,970 cm$^{-1}$ (C—H),
2,250 cm$^{-1}$ (Si—H),
1,260 cm$^{-1}$ (Si—CH$_3$),
1,250–1,050 cm$^{-1}$ (CF$_2$, CF$_3$),
1,120–1,050 cm$^{-1}$ (Si—O)

| GPC (toluene), molecular weight converted into polystyrene | |
|---|---|
| number-average molecular weight (Mn) | 12,320 |
| weight-average molecular weight (Mw) | 13,550 |
| polydispersion degree (Mw/Mn) | 1.1 |
| Quantitation Data of Si—H group: H (ppm) | 99.3 |
| calculated molecular weight from H (ppm) | 10,070 |
| Viscosity (25° C.): | 172 centipoises |

Example 10

Preparation of dimethylsiloxane compound with a tridecafluoro-1,1,2,2-tetrahydrooctyl group at its α-position and a —CH$_2$CH$_2$CH$_2$(OCH$_2$CH$_2$)$_7$—OH group at its ω-position A 2-liter three-necked round flask with a stirrer and a cooler was charged with 100.7 g of the siloxane compound prepared in Reference Example 10 and 400 ml of toluene and heated to 100° C. After $5.2 \times 10^{-4}$ g ($1.0 \times 10^{-6}$ mol) of chloroplatinic acid was added, 4.8 g (0.011 mol) of CH$_2$=CHCH$_2$(OCH$_2$CH$_2$)$_7$—OSi(CH$_3$)$_3$ (after "Uniox PKA-500" (Nihon Yushi K.K.) was silylated, isolated and purified by distillation) was added. The mixture was maintained at the reaction temperature of 100° C. for 20 hours and then subjected to a reaction for removing a trimethylsilyl group using 500 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and hydroxy group quantitation data are as shown below.

The resulting product was identified as having the following formula:

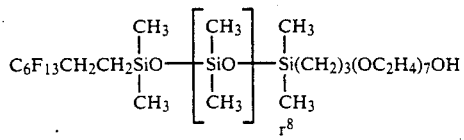

IR (KBr):
3,650–3,200 cm$^{-1}$ (—OH),
2,970 cm$^{-1}$ (C—H),
1,260 cm$^{-1}$ (Si—CH$_3$),
1,250–1,150 cm$^{-1}$ (CF$_2$, CF$_3$),
1,120–1,050 cm$^{-1}$ (Si—O)

| GPC (toluene), molecular weight converted into polystyrene | |
|---|---|
| number-average molecular weight (Mn) | 11,400 |
| weight-average molecular weight (Mw) | 13,700 |
| polydispersion degree (Mw/Mn) | 1.2 |
| Quantitation Data of OH group: OH (% by weight) | 0.16 |
| calculated molecular weight from OH (% by weight) | 10,630 |
| Viscosity (25° C.): | 241 centipoises |

Example 11

Preparation of dimethylsiloxane compound with a tridecafluoro-1,1,2,2-tetrahydrooctyl group at its α-position and a 3-(o-hydroxyphenyl)propyl group at its ω-position A 2-liter three-necked round flask with a stirrer and a cooler was charged with 100.7 g of the siloxane compound prepared in Reference Example 10 and 300 ml of toluene and heated to 80° C. After $5.2 \times 10^{-5}$ g ($1.0 \times 10^{-7}$ mol) of chloroplatinic acid was added, 1.5 g (0.011 mol) of o-(2-propenyl)phenol. The mixture was maintained at the reaction temperature of 80° C. for 20 hours.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and hydroxy group quantitation data are as shown below.

IR (KBr):
3,650–3,200 cm$^{-1}$ (—OH),
2,970 cm$^{-1}$ (C—H),
1,260 cm$^{-1}$ (Si—CH$_3$),
1,250–1,150 cm$^{-1}$ (CF$_2$, CF$_3$),
1,120–1,050 cm$^{-1}$ (Si—O),
750 cm$^{-1}$ (  , 1,2-disubstituted)

| GPC (toluene), molecular weight converted into polystyrene | |
|---|---|
| number-average molecular weight (Mn) | 11,950 |
| weight-average molecular weight (Mw) | 14,220 |
| polydispersion degree (Mw/Mn) | 1.2 |
| Quantitation Data of OH group: OH (% by weight) | 0.17 |
| calculated molecular weight from OH (% by weight) | 10,000 |
| Viscosity (25° C.): | 310 centipoises |

The polyorganosiloxane compounds according to the present invention may provide the following advantages when they are chemically incorporated into a synthetic resin having reactive groups, such as polyurethane, polyester or the like.

(1) As the reactive group or groups of the polyorganosilane compound is or are chemically bonded to the synthetic resin such as polyurethane, polyester or the like, a reduction in characteristics can be prevented even if time passes by.

(2) As the fluoroalkyl group resides in the same molecule, the polyorganosiloxane compounds according to the present invention provide the synthetic resins with various characteristics such as repellency against water, oil or snow, an anti-fouling property, mold releasability, non-adhesion, and low friction properties, which conventional polysiloxane compounds with a trimethylsiloxy group at its terminal cannot provide, or better than those conventional polysiloxane compounds can provide, without impairing the various functions of the polyorganosiloxane compounds.

(3) As the polyorganosiloxane compounds according to the present invention, in a preferable case, has a distribution of molecular weights within a range as narrow as from 1.1 to 1.2, their molecular chains are said to be relatively equal in length so that the synthetic resin into which such a polyorganosiloxane compound is introduced can provide a modified resin with a more uniform structure than a polysiloxane compound having molecular chains having different length. In addition, the polyorganosiloxane compounds cause no production of a cyclic dimethylsiloxane that cannot be removed, which could not be avoided by the equilibrium reaction by means of a conventional acidic or basic catalyst, thereby preventing a reduction of characteristics, bleeding and a fluctuation in quality between products on account of the cyclic by-product and improving the properties of the resulting products.

(4) In using the polyorganosiloxane compounds according to the present invention as a graft polymer for improvements in various functions and characteristics of the synthetic resin, such as water and oil repellency, anti-fouling property, mold releasability, non-adhesion and low frictional properties, they can provide the synthetic resin with the properties of the siloxane compound and, in addition thereto, with the peculiar functions inherent in the fluoroalkyl group thereof. The polyorganosiloxane compound enables the provision of the synthetic resin with a relatively uniform structure and, furthermore, a control over the characteristics of the resulting synthetic resin by changing the length of molecular chains of the siloxane moiety and the fluoroalkyl moiety in accordance with usage. Thus, as compared with the conventional dimethylsiloxane compound of the type having no fluoroalkyl group, the polyorganosiloxane compounds permits a wide application of the synthetic resins to usage requiring high performance, particularly surface modification. Such characteristics can be realized by the polyorganosiloxane compound in a lesser amount than the conventional siloxane compound so that an adverse influence of the siloxane upon the basic properties of the synthetic resin can be blocked to a maximum extent.

(5) As the number of siloxane chains of the polyorganosiloxane compound on the basis of the hydrosilyl group reactive with the synthetic resin can be selected arbitrarily from one to three, as a length of the siloxane chains can be changed, and as the kind of the fluorine-containing group residing in the siloxane chain at its terminal can be determined, in accordance with demands, the functions required by the objective synthetic resin can be provided in a sensitively controlled manner.

(6) In addition to item (5) above, a compatibility of the polyorganosiloxane compound with the synthetic resin can be conveniently raised by changing a length of the molecular chain of the alkylene oxide in the hydrosilyl site and the kind of the alkylene oxde, thereby enabling a uniform introduction of the polyorganosiloxane compound into the synthetic resin.

(7) A reactivity of the polyorganosiloxane compound upon introduction into the synthetic resin can be changed because of the number and the kind, primary or secondary, of terminal hydroxyl groups.

It is to be understood that the present invention may be embodied in other specific forms without departing from the spirit and scope thereof. The present embodiments are therefore to be considered in all respects as illustrative and not restrictive, the scope of the invention being indicated by the appended claims, and all the changes, modifications and variations which come within the meaning and range of equivalency of the claims are therefore intended to be encompassed within the spirit and scope of the invention.

What is claimed is:

1. A polyorganosiloxane compound represented by the following general formula (I):

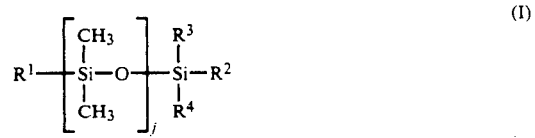

in which
j is an integer from 2 to 2,000;
$R^1$ is a pentafluorophenyl group or a linear or branched fluoroalkyl group as represented by the following general formula (II):

$$C_aH_bF_{2a-b+1} \qquad (II)$$

wherein
a is an integer from 3 to 18; and
b is 0 or an integer of 2a
$R^2$ is 3-(m-hydroxyphenyl)propyl group, 3-(o-hydroxyphenyl)propyl group, 3-(p-hydroxyphenyl)propyl group, a substituent as represented by the general formula (III):

wherein
$h^0$ is an integer from 1 to 6; and
$h^1$ and $h^2$ are independently each 0 or an integer from 1 to 20,
a substituent as represented by the following general formula (IV):

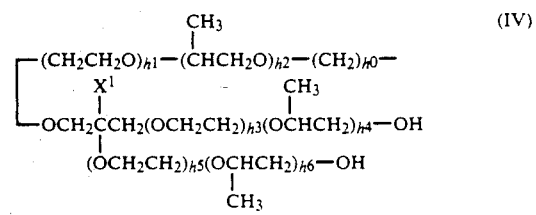

wherein
$X^1$ is a hydrogen atom, methyl group or ethyl group;
$h^3$, $h^4$, $h^5$ and $h^6$ are independently 0 or an integer from 1 to 20; and $h^0$, $h^1$ and $h^2$ have the same meanings as above, or a substituent as represented by the following general formula (V):

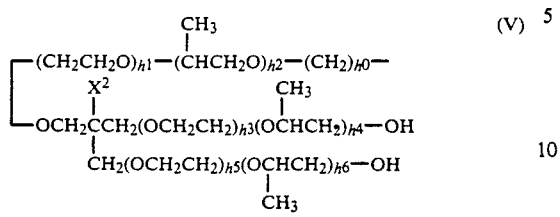

wherein
$X^2$ is a hydrogen atom, methyl group or ethyl group; and
$h^1$, $h^2$, $h^3$, $h^4$, $h^5$ and $h^6$ have the same meanings as above; and
$R^3$ and $R^4$ are independently each an alkyl group having from 1 to four carbon atoms or a phenyl group.

2. A polyorganosiloxane compound as claimed in claim 1, wherein the substituent represented by the symbol $R^1$ is 3,3,3-trifluoropropyl group, tridecafluoro-1,1,2,2-tetrahydrooctyl group or heptadecafluoro-1,1,2,2-tetrahydrodecyl group.

3. A polyorganosiloxane compound as represented by the following general formula (VI):

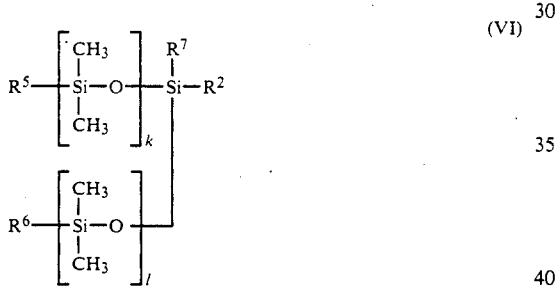

in which
k and l each is an integer from 2 to 2,000;
$R^5$ and $R^6$ are independently each an alkyl group having from 1 to 4 carbon atoms, pentafluorophenyl group or a linear or branched fluoroalkyl group as represented by the following general formula (II):

$$C_aH_bF_{2a-b+1} \quad (II)$$

wherein
a is an integer from 3 to 18; and
b is 0 or an integer of 2a,
provided, however, that at least one of $R^5$ and $R^6$ is the pentafluorophenyl group or the fluroalkyl group;
$R^2$ is 3-(m-hydroxyphenyl)propyl group, 3-(o-hydroxyphenyl)propyl group, 3-(p-hydroxyphenyl)propyl group, a substituent as represented by the general formula (III):

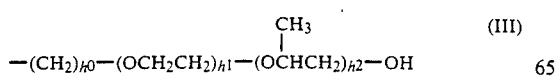

$$-(CH_2)_{h0}-(OCH_2CH_2)_{h1}-(OCHCH_2)_{h2}-OH \quad (III)$$
$$\overset{|}{CH_3}$$

wherein
$h^o$ is an integer from 1 to 6; and $h^1$ and $h^2$ are independently each 0 or an integer from 1 to 20,
a substituent as represented by the following general formula (IV):

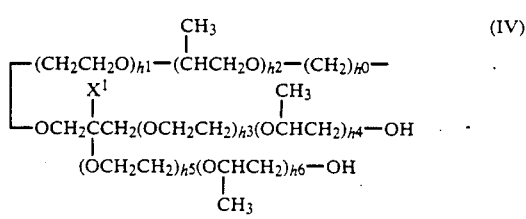

wherein
$X^1$ is a hydrogen atom, methyl group or ethyl group;
$h^3$, $h^4$, $h^5$ and $h^6$ are independently 0 or an integer from 1 to 20; and
$h^0$, $h^1$ and $h^2$ have the same meanings as above, or a substituent as represented by the following general formula (V):

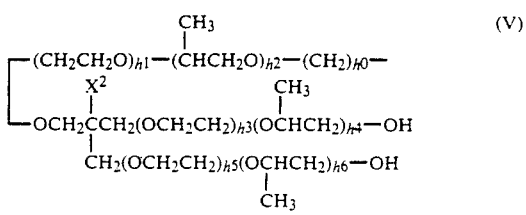

wherein
X is a hydrogen atom, methyl group or ethyl group; and
$h^0$, $h^1$, $h^2$, $h^3$, $h^4$, $h^5$ and $h^6$ have the same meanings as above; and
$R^7$ is an alkyl group having 1 to four carbon atoms or a phenyl group.

4. A polyorganosiloxane compound as claimed in claim 3, wherein the substituents represented by the symbols $R^5$ and $R^6$ in the general formula (VI) are independently each an alkyl group having 1 to four carbon atoms, 3,3,3-trifluoropropyl group, tridecafluoro-1,1,2,2-tetrahydrooctyl group or heptadecafluoro-1,1,2,2-tetrahydrodecyl.

5. A polyorganosiloxane compound as represented by the following general formula:

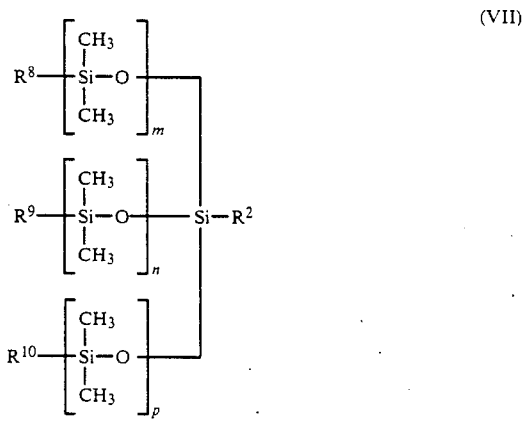

in which m, n and p each independently is an integer from 2 to 2,000;

$R^8$, $R^9$ and $R^{10}$ are independently each an alkyl group having from 1 to 4 carbon atoms, a pentafluorophenyl group or a linear or branched fluoroalkyl group as represented by the following general formula (II):

$$C_aH_bF_{2a-b+1} \quad (II)$$

wherein a is an integer from 3 to 18; and b is 0 or an integer of 2a, provided, however, that at least one of $R^8$, $R^9$ and $R^{10}$ is the pentafluorophenyl group or the fluroalkyl group;

$R^2$ is 3-(m-hydroxyphenyl)propyl group, 3-(o-hydroxyphenyl)propyl group, 3-(p-hydroxyphenyl)propyl group, a substituent as represented by the general formula (III):

$$-(CH_2)_{h0}-(OCH_2CH_2)_{h1}-(O\overset{CH_3}{\underset{|}{C}}HCH_2)_{h2}-OH \quad (III)$$

wherein $h^0$ is an integer from 1 to 6; and $h^1$ and $h^2$ are independently each 0 or an integer from 1 to 20, a substituent as represented by the following general formula (IV):

$$\begin{array}{l}\left[\begin{array}{l}-(CH_2CH_2O)_{h1}-(\overset{CH_3}{\underset{|}{C}}HCH_2O)_{h2}-(CH_2)_{h0}-\\ \phantom{-}\overset{X^1}{\underset{|}{\phantom{O}}}\phantom{CCH_2(OCH_2CH_2)_{h3}}\overset{CH_3}{\underset{|}{\phantom{O}}}\\ -OCH_2\overset{|}{C}CH_2(OCH_2CH_2)_{h3}(O\overset{|}{C}HCH_2)_{h4}-OH\\ \phantom{-OCH_2}\overset{|}{(OCH_2CH_2)_{h5}CHCH)_{2h6}-OH}\\ \phantom{-OCH_2CCH_2(OCH_2CH)}\overset{|}{CH_3}\end{array}\right.\end{array} \quad (IV)$$

wherein $X^1$ is a hydrogen atom, methyl group or ethyl group;

$h^3$, $h^4$, $h^5$ and $h^6$ are independently 0 or an integer from 1 to 20; and $h^0$, $h^1$ and $h^2$ have the same meanings as above, or a substituent as represented by the following general formula (V):

$$\left[\begin{array}{l}-(CH_2CH_2O)_{h1}-(\overset{CH_3}{\underset{|}{C}}HCH_2O)_{h2}-(CH_2)_{h0}-\\ \phantom{-}\overset{X^2}{\underset{|}{\phantom{O}}}\phantom{CCH_2(OCH_2CH_2)_{h3}}\overset{CH_3}{\underset{|}{\phantom{O}}}\\ -OCH_2\overset{|}{C}CH_2(OCH_2CH_2)_{h3}(O\overset{|}{C}HCH_2)_{h4}-OH\\ \phantom{-OCH_2}CH_2(OCH_2CH_2)_{h5}(O\overset{|}{C}HCH_2)_{h6}-OH\\ \phantom{-OCH_2CCH_2(OCH_2CH)}\overset{|}{CH_3}\end{array}\right. \quad (V)$$

wherein $X^2$ is a hydrogen atom, methyl group or ethyl group; and $h^0$, $h^1$, $h^2$, $h^3$, $h^4$, $h^5$ and $h^6$ have the same meanings as above.

6. A polyorganosiloxane compound as claimed in claim 5, wherein the substituents as represented by the reference symbols $R^8$, $R^9$ and $R^{10}$ of the general formula (VII) each independently is an alkyl group having from 1 to four carbon atoms, 3,3,3-trifluoropropyl, tridecafluoro-1,1,2,2-tetrahydrooctyl group or heptadecafluoro-1,1,2,2-tetrahydrodecyl group and at least one of $R^8$, $R^9$ and $R^{10}$ is the fluorine-containing substituent selected from the above substituents.

7. A polyorganosiloxane compound as claimed in claim 1, wherein the substituent as represented by the reference symbol $R^2$ is:

$$-(CH_2)_3-OCH_2CH_2-OH$$

8. A polyorganosiloxane compound as claimed in claim 2, wherein the substituent as represented by the reference symbol $R^2$ is:

$$-(CH_2)_3-OCH_2CH_2-OH$$

9. A polyorganosiloxane compound as claimed in claim 3, wherein the substituent as represented by the reference symbol $R^2$ is:

$$-(CH_2)_3-OCH_2CH_213\ OH$$

10. A polyorganosiloxane compound as claimed in claim 4, wherein the substituent as represented by the reference symbol $R^2$ is:

$$-(CH_2)_3-OCH_2CH_2-OH$$

11. A polyorganosiloxane compound as claimed in claim 5, wherein the substituent as represented by the reference symbol $R^2$ is:

$$-(CH_2)_3-OCH_2CH_2-OH$$

12. A polyorganosiloxane compound as claimed in claim 6, wherein the substituent as represented by the reference symbol $R^2$ is:

$$-(CH_2)_3-OCH_2CH_2-OH$$

13. A polyorganosiloxane compound as claimed in claim 1, wherein the substituent as represented by the reference symbol $R^2$ is:

$$-(CH_2)_3-OCH_2\overset{X^1}{\underset{\underset{OH}{|}}{C}}CH_2-OH$$

wherein $X^1$ is a hydrogen atom, methyl group or ethyl group.

14. A polyorganosiloxane compound as claimed in claim 2, wherein the substituent as represented by the reference symbol $R^2$ is:

$$-(CH_2)_3-OCH_2\overset{X^1}{\underset{\underset{OH}{|}}{C}}CH_2-OH$$

wherein $X^1$ is a hydrogen atom, methyl group or ethyl group.

15. A polyorganosiloxane compound as claimed in claim 3, wherein the substituent as represented by the reference symbol $R^2$ is:

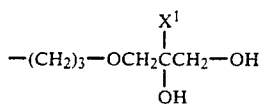

wherein $X^1$ is a hydrogen atom, methyl group or ethyl group.

16. A polyorganosiloxane compound as claimed in claim 4, wherein the substituent as represented by the reference symbol $R^2$ is:

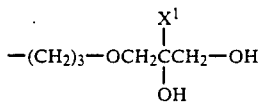

wherein $X^1$ is a hydrogen atom, methyl group or ethyl group.

17. A polyorganosiloxane compound as claimed in claim 5, wherein the substituent as represented by the reference symbol $R^2$ is:

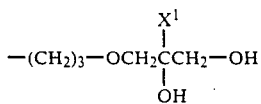

wherein $X^1$ is a hydrogen atom, methyl group or ethyl group.

18. A polyorganosiloxane compound as claimed in claim 6, wherein the substituent as represented by the reference symbol $R^2$ is:

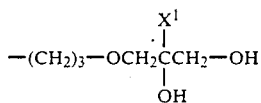

wherein $X^1$ is a hydrogen atom, methyl group or ethyl group.

19. A polyorganosiloxane compound as claimed in claim 1, wherein the substituent as represented by the reference symbol $R^2$ is:

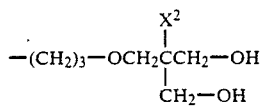

wherein $X^2$ is a hydrogen atom, methyl group or ethyl group.

20. A polyorganosiloxane compound as claimed in claim 2, wherein the substituent as represented by the reference symbol $R^2$ is:

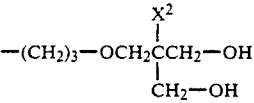

wherein $X^2$ is a hydrogen atom, methyl group or ethyl group.

21. A polyorganosiloxane compound as claimed in claim 3, wherein the substituent as represented by the reference symbol $R^2$ is:

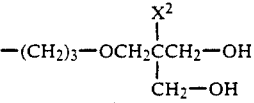

wherein $X^2$ is a hydrogen atom, methyl group or ethyl group.

22. A polyorganosiloxane compound as claimed in claim 4, wherein the substituent as represented by the reference symbol $R^2$ is:

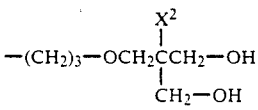

wherein $X^2$ is a hydrogen atom, methyl group or ethyl group.

23. A polyorganosiloxane compound as claimed in claim 5, wherein the substituent as represented by the reference symbol $R^2$ is:

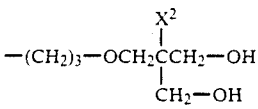

wherein $X^2$ is a hydrogen atom, methyl group or ethyl group.

24. A polyorganosiloxane compound as claimed in claim 6, wherein the substituent as represented by the reference symbol $R^2$ is:

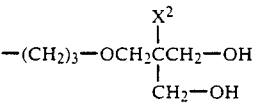

wherein $X^2$ is a hydrogen atom, methyl group or ethyl group.

* * * * *

UNITED STATES PATENT AND TRADEMARK OFFICE
CERTIFICATE OF CORRECTION

PATENT NO. : 5,047,491

DATED : September 10, 1991

INVENTOR(S) : Saho et al

It is certified that error appears in the above-identified patent and that said Letters Patent is hereby corrected as shown below:

Column 31, line 17, before "$h^1$" insert --$h^0$,--.

Column 34, line 23, delete "13".

Signed and Sealed this

Second Day of March, 1993

Attest:

STEPHEN G. KUNIN

Attesting Officer

Acting Commissioner of Patents and Trademarks